US006682488B2

(12) United States Patent
Abend

(10) Patent No.: US 6,682,488 B2
(45) Date of Patent: Jan. 27, 2004

(54) ULTRASOUND PROBE WITH PROGRESSIVE ELEMENT SIZING

(75) Inventor: Kenneth Abend, Huntingdon Valley, PA (US)

(73) Assignee: Vuesinx Sensors, Inc., Wayne, PA (US)

( * ) Notice: Subject to any disclaimer, the term of this patent is extended or adjusted under 35 U.S.C. 154(b) by 312 days.

(21) Appl. No.: 09/834,002

(22) Filed: Apr. 12, 2001

(65) Prior Publication Data

US 2002/0151790 A1 Oct. 17, 2002

(51) Int. Cl.[7] .................................................. A61B 8/06
(52) U.S. Cl. ...................................................... 600/453
(58) Field of Search ................................. 600/437, 440, 600/441, 442–447, 453–459, 439; 367/7, 11, 103; 310/324, 311, 334, 338, 339, 366, 800; 73/625; 601/2, 3; 128/916; 342/179

(56) References Cited

U.S. PATENT DOCUMENTS

| 5,278,757 A | * | 1/1994 | Hoctor et al. ................ 600/459 |
| 5,406,163 A | * | 4/1995 | Carson et al. ............... 310/334 |
| 5,787,049 A | * | 7/1998 | Bates ............................ 367/7 |
| 5,808,962 A | * | 9/1998 | Steinberg et al. ............... 367/7 |
| 5,911,692 A | * | 6/1999 | Hussain et al. ............. 600/447 |
| 6,135,971 A | * | 10/2000 | Hutchinson et al. ........... 601/3 |

FOREIGN PATENT DOCUMENTS

| WO | US00/14691 | 5/2000 |
| WO | US00/16536 | 6/2000 |

* cited by examiner

Primary Examiner—Ali N. Imam
(74) Attorney, Agent, or Firm—McCarter & English LLP; Allen M. Friedman; Christine Johnson

(57) ABSTRACT

A prior application discloses a novel probe geometry that offers a wide field of view in an ultrasonic imaging device. That geometry is referred to as a "thinned array" of transducer elements. The application discloses an improved probe geometry permitting high-resolution imaging of a large volume of the subject's body. In this improved geometry, the array elements are non-uniform in size and spacing. The probe is intended for use, for example, in a method of determining parameters of blood flow, such as vector velocity, blood flow volume, and Doppler spectral distribution, using sonic energy (ultrasound) and a novel thinned array. Also in a method of tracking blood flow and generating a three dimensional image of blood vessel of interest that has much greater resolution than images produced using heretofore known ultrasound devices and methods.

4 Claims, 7 Drawing Sheets

$x = (d/\lambda) \sin \theta$

ULTRASOUND PROBE WITH PROGRESSIVE ELEMENT SIZING

BACKGROUND OF THE INVENTION

1. Field of the Invention

The present invention involves an ultrasound Doppler method that permits non-invasive diagnosis and non-invasive unattended, continuous monitoring of vascular blood flow for medical applications.

2. Brief Description of the Background Art

Acoustic Doppler blood velocity measurement is a known medical diagnostic tool. The phased array steering of the acoustic beam and the phased array listening for the Doppler frequency-shifted echo are techniques that derive from a large body of work in the field of phased-array radar systems. The Doppler frequency shifts result from reflection of the transmitted acoustic beam from the moving blood constituents and are related in a known way to the velocity of blood flows. However, blood velocity monitoring is not currently practical for intensive care unit (ICU) of surgical applications. For non-invasive brain blood velocity monitoring, for example, a transcranial Doppler (TCD) probe must be mounted in a ball joint that is attached to the head by a helmet. The probe must be carefully aimed and fastened in place by an experienced person who knows how to locate the middle cerebral artery. Slight movements cause the probe to lose the blood velocity signal. Moreover, conventional Doppler ultrasound probes used in these devices scan (either mechanically or by using an acoustic phased array) in only one angle (which we will call azimuth), and will map only a single slice of the object being imaged. Efforts have been made to modify such devices to provide real-time three dimensional (3-D) imaging. However, in order for a two dimensional (2-D) device to provide such imaging normally requires thousands of elements, and must form many thousands of pencil beams every 1/30 second. Sensor cost grows with the number of elements in the array and the number of processing channels. Thus, such devices are cost prohibitive, as well as impractical.

Moreover, no automated procedure exists in current practice for precisely locating the optimum point at which to measure the Doppler signal. Conventional ultrasound Doppler-imaging devices can only measure radial velocity in blood vessels, i.e., the velocity component parallel to the ultrasound wave direction, and not the vector velocity parallel to the blood vessel or the magnitude of the velocity of the blood through the vessel. Accordingly, what is needed is a new and useful Doppler ultrasound device method that can automatically locate the optimum point at which to measure the Doppler signal, and thus provide medical providers with parameters such as vector velocity, the volume of blood passing through the blood vessel and the Doppler spectral distribution of the blood flow and make those measurements over a large field of view for a single probe placement.

SUMMARY OF THE INVENTION

Copending applications PCT/US00/14691 and PCT/US00/16535 disclose a method of determining parameters of blood flow, such as vector velocity, blood flow volume, and Doppler spectral distribution, using sonic energy (ultrasound) and a novel thinned array. Also provided is a novel method of tracking blood flow and generating a three dimensional image of blood vessel of interest that has much greater resolution than images produced using heretofore known ultrasound devices and methods. The second of the above referenced applications discloses a novel probe geometry that offers a wide field of view. That geometry is referred to as a "thinned array" of transducer elements. Broadly, the present invention discloses an improved probe geometry permitting high-resolution imaging of a large volume of the subject's body. In this improved geometry, the array elements are non-uniform in size and spacing.

A phased array will be referred to as thinned if its elements are spaced more than one half wavelength between centers. It will be referred to as sparse (or not filled) if there is space between the elements. A non-sparse (or filled) thinned array therefore has directive elements whose size is equal to the spacing between centers. Such an array is well behaved when focused at infinity and steered to broadside. This is because such an array becomes a continuous (no space between elements), uniformly illuminated, aperture. If the elements were narrow-band and omni-directional, the grating lobes, due to a path-length change corresponding to a $2\pi$ phase shift, would be true ambiguities, indistinguishable from the main lobe or desired focus. When a filled, thinned array of uniformly-spaced equal-sized elements is uniformly illuminated (no element-to-element delays or phase shifts), the nulls of the element pattern coincide with the ambiguities of the far-field array pattern. The non ambiguous element pattern multiplies the ambiguous array pattern to reduce the grating lobes. See Patent Application No. PCT/US00/16535. When the array is either steered away from broadside or focused in the near field, ambiguities, called grating lobes, begin to appear. For example, if the array is steered or focused to the right, the desired beam is attenuated because it moves to the right, away from the peak of the element pattern and, more importantly, the nearest grating lobe on the left begins to move toward the peak of the element pattern. This limits the angular field of view of a thinned phased array, even if it is filled.

BRIEF DESCRIPTION OF THE DRAWINGS

FIG. 1B shows the second, or alternative, transmitter array. The diamond (smaller rotated) transmitters produce a $(\sin x/x)^2$ pattern in azimuth and in elevation as shown in FIG. 3A.

FIG. 3B shows a cluster of eight receiver beams along with the grating lobes of a thinned receiver array. FIG. 3A shows the $(\sin \pi x/\pi x)^2$ triangularly weighted transmitter. FIG. 3C shows the resultant two-way beam pattern with grating lobes suppressed. The two-dimensional counterpart of FIG. 3 would use an 8×8 array of diamond-shaped uniformly weighted transmitters and a 16 by 16=256 element planar receive array. This would produce an 8 by 8 cluster of 64 received beams.

DETAILED DESCRIPTION OF THE INVENTION

Figure 1:
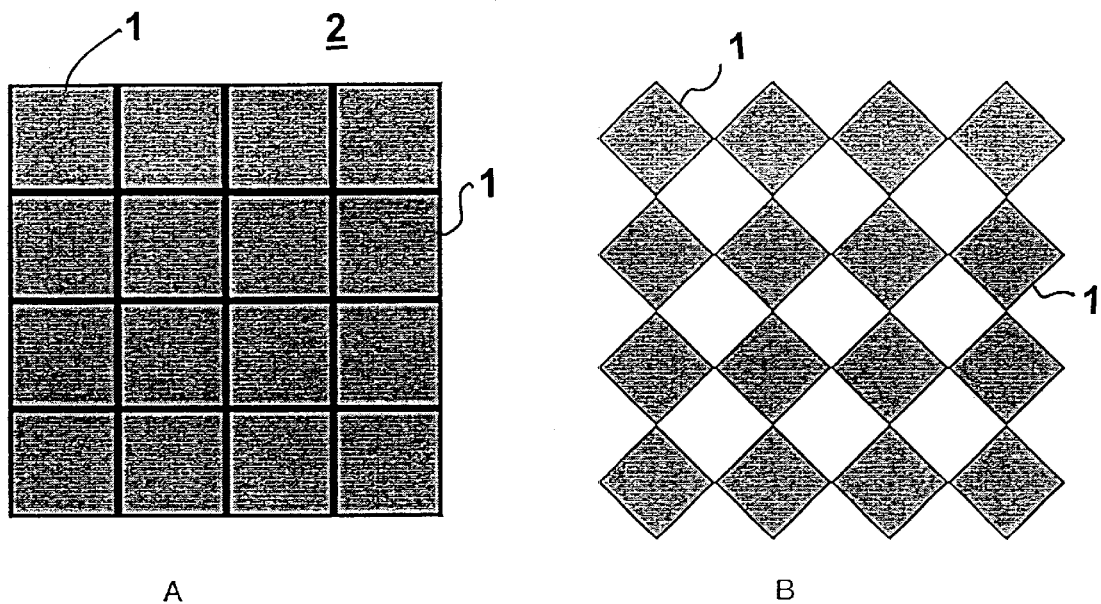
FIG. 1 shows two possible N/r by M/s arrays of transmitters corresponding to an N by M receiver array, illustrated for the Case N/r=M/s=4. Each square or diamond represents a single transmitter. E.g., N=M=8 and r=s=2. The rectangular transmitter of FIG. 1A produces the sin x/x Pattern in Azimuth and in Elevation Shown in FIG. 2.

A uniformly spaced thinned array, as used in the system disclosed in PCT/US00/14691, comprises:
 (a) a plurality of transmitters configured so that one transmitter insonates one individual segment of the volume at a time; and
 (b) an array of receivers that simultaneously receive echoes from the volume being evaluated, wherein the array of receivers is electronically aimed and dynamically focused upon sub-segments of the insonated segment of the volume, wherein the spacing among the receivers in the array is greater than one half the wavelength of the ultrasound energy produced by the transmitters, and the receivers are configured to receive echoes from the sub-segments of the individual insonated segments of the volume of the subject's body in a pattern that is aligned with the insonated segment of the volume insonated by the transmitters, so that receiver grating lobes nearest the echoes coincide with first transmitter nulls, and the deleterious effects of grating lobes are minimized.

As used herein the phrase "electronically aimed" with respect to an array of receivers or transmitters of a thinned array of the present invention means that phase shifts or delays are applied to the individual elements so that a beam is steered or focused on a particular segment or sub-segment of the volume of the subject being evaluated.

As used herein, the phrase "dynamically focused" with respect to transducers of a thinned array of the present invention means that the phase shifts can vary with time so as to depend on range or depth. This takes place during analysis of the signals received by each of the receiving transducers.

The angular resolution nominal beamwidth (in radians) of an N-element phased array with uniform element spacing, d, is b=1/(Nd). If the element spacing is non-uniform, this same relation holds with d replaced by the mean (average) spacing because it is the total array size, D=Nd, that determines the resolution. The angular field of view is now increased because, with non-uniform spacing, the grating lobes of the filled array are no longer at a single point. The $2\pi$ ambiguity leading to a grating lobe no longer occurs at one particular location. The signals from these grating lobes are smeared out so that the desired central lobe is more easily detected.

As used herein, the phrases "element spacing" and "distance between the elements" can be used interchangeably and refer to the distance between the centers of the elements of an array.

Various methods can be used to determine the three-dimensional position of blood flow. In a particular embodiment, the method comprises the steps of having the processor programmed to:
 i) determine a sum beam, an azimuth difference beam and an elevation difference beam from the Doppler-shifted echoes received from the blood vessel of interest;
 ii) modulate the directions of the transmitted and received sonic energy based upon the sum, azimuth difference and elevation difference beams in order to lock onto the highest Doppler energy calculated from echoes from the flow of blood in the blood vessel of interest, and
 iii) calculate the three-dimensional position of the highest Doppler energy from the blood flow in the vessel of interest.

Optionally, the processor can also be programmed to determine at least one additional beam having an angle between the azimuth difference beam and the elevation difference beam prior to modulating the directions of the transmitted and received sonic energy, wherein the at least one additional beam is used to modulate the directions of the transmitted and received sonic energy. Naturally, the angle of the at least one additional beam can vary. In a particular embodiment, the at least one additional beam is at an angle that is orthogonal to the blood vessel of interest.

Moreover, steps (b) through (e) can be periodically repeated so that the three dimensional position of blood flow in the vessel of interest is tracked, and the parameter of blood flow is periodically calculated and displayed on the display monitor. In a particular embodiment, the period of time between repeating steps (b) through (e) is sufficiently short so that the parameter being measured remains constant, e.g., 20 milliseconds.

The basic method for determining a parameter of blood flow in a particular region of a blood vessel of interest, comprises the steps of:
 a) providing an array of sonic transducer elements, wherein the element spacing in the array is greater than, a half wavelength of the sonic energy produced by the elements, wherein at least one element transmits sonic energy, and a portion of the elements receive sonic energy;
 b) directing sonic energy produced by the at least one element of the array into a volume of the subject's body having the particular region of the blood vessel of interest;
 c) receiving echoes of the sonic energy from the volume of the subject's body having the particular region of the blood vessel of interest;
 d) reporting the echoes to a processor programmed to:
  i) Doppler process the echoes to determine radial velocity of the blood flowing in the particular region of the blood vessel of interest;
  ii) calculate a three dimensional position of blood flow in the particular region of the blood vessel of interest; and
  iii) calculate the parameter of blood flow in the particular region of the blood vessel of interest at the three dimensional position calculated in step (ii); and
 (e) displaying the parameter on a display monitor that is electrically connected to the processor.

A particular method of calculating the three dimensional position of blood flow in such a method of the present invention comprises having the processor programmed to:

i) determine a sum beam, an azimuth difference beam and an elevation difference beam from the echoes received from the blood vessel of interest;

ii) modulate the directions of the transmitted and received sonic energy based upon the sum, azimuth difference and elevation difference beams in order to lock onto the highest Doppler energy calculated from echoes from the flow of blood in the blood vessel of interest, and iii) calculate the three-dimensional position of the highest Doppler energy from the blood flow in the vessel of interest.

As explained above, at least one additional beam can also be determined and used to calculate the three dimensional position.

In a particular embodiment, the transmitters and receivers of a thinned array of the present invention are in a two-dimensional configuration. The shape of the transmitters can vary. Particular examples include, but certainly are not limited to rectangles, e.g., a square, and diamond shapes. In an embodiment wherein the transmitters are rectangular in shape, the transmitters are positioned flush against each other.

As explained above, a thinned array of the present invention also comprises a plurality of receivers that simultaneously receive echoes from the volume being evaluated, wherein the spacing of the receivers is greater than ½ the wavelength of the sonic energy produced by the transmitters. In a particular embodiment of the present invention, wherein the transmitters are diamond in shape, the receivers can optionally be interleaved with the transmitters.

Naturally, a thinned array of the present invention is electronically connected to a particular ultrasound device utilizing the thinned array.

Thus, a thinned (greater than ½ wavelength element spacing) array of ultrasound transducers of the present invention is used to form a large number of received and focused beams within an insonated volume. The signals received in each transducer are stored and analyzed to form the received and focused beams using the detected phase shift in each data stream relative to the common clock. Since array thinning allows for scanning or imaging over only a limited region or segment, a set of transmitters are fired one at a time to insonate one segment at a time. The receiver is an array of receiver elements, all receiving simultaneously echoes from the volume of the subject's body insonated by the transmitters one at a time. A novel aspect of the present invention, wherein each particular transmitter insonates a segment of the volume subject's body, permits the insonation and evaluation of a larger volume the subject's body than can be evaluated with heretofore known thinner arrays. A large number of receive beams are formed digitally for each transmitted pulse.

The present invention is based upon the discovery that surprisingly and unexpectedly, a thinned array for use with an ultrasound device can be designed with progressive element sizing that permits evaluation of a large volume of a subject's body, and increases the number of resolution elements of ultrasound images obtained as compared with images obtained with heretofore known arrays.

Numerous terms and phrases are used throughout the instant specification and appended claims. As used herein, the phrase "element spacing" or "spacing" can be used interchangeably and refer to the distance between the center of receivers or transmitters of a thinned array of the present invention. In one embodiment of the present invention described above, the spacing between transmitters is greater than ½ the wavelength of ultrasonic energy produced by the transmitters. In another embodiment described above, the spacing between the receivers is greater than ½ the wavelength of the ultrasonic energy produced by the transmitters.

As used herein, the phrase "electronically aimed" with respect to an array of receivers or transmitters of a thinner array of the present invention means that phase shifts or delays are applied to the individual elements so that a beam is steered or focused on a particular segment or sub-segment of the volume of the subject being evaluated. Also, the phrase "dynamically focused" with respect to transducers of a thinned array of the present invention means that the phase shifts can vary with time so as to depend on range or depth.

In addition, the phrase "first transmitter nulls" as used herein refers to places nearest the insonated segment of the volume of the subject's body being evaluated where the transmitter power is zero or near zero. The phrase "transmitter sidelobe patterns" refers to the angular distribution of transmitted energy outside the segment intentionally insonated. And the terms "transducer" and "element" refer to transmitters and/or receivers of ultrasonic energy.

Hence, contrary to heretofore known thinned arrays for use with ultrasound devices, an embodiment of a thinned array, as described above, utilizes set of dedicated transmit apertures, each permanently aimed in a different direction. If, for example, the receive array is to be electronically scanned over the entire 90° by 90° sector, the receiver array elements must be wide-angle, covering an entire octant without significant attenuation.

In another embodiment of a thinned array, dedicated receiver apertures are used, and the transmitter array is thinned as described herein.

EXAMPLE

Figure 2:
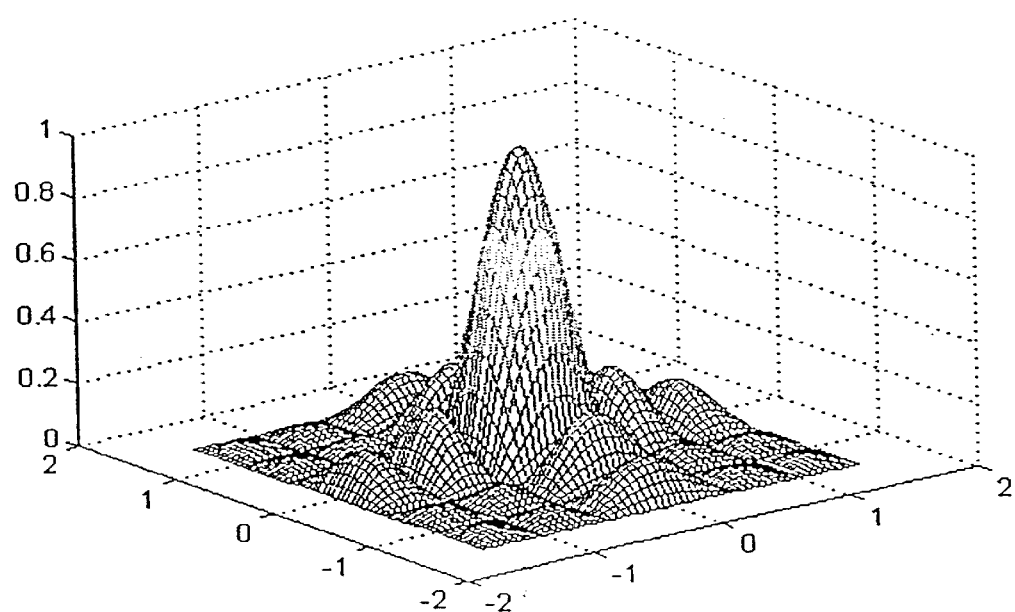
FIG. 2 shows a two-dimensional sin $(2\pi x)/2\pi x$ pattern due to a uniformly weighted rectangular aperture as in FIG. 1A. Rotating and shrinking the aperture as shown in FIG. 1B rotates and expands the pattern. The resulting pattern is $(\sin \pi x/\pi x)^2$ in both azimuth and elevation as shown in FIG. 3A. This pattern can also be achieved by applying a triangular shading (amplitude weight taper) across the original (FIG. 1A) rectangular transmitter aperture. By way of example, assume the width (or height) of each transmitter is $2d$, where $d$ is the spacing between elements in the N by M rectangular receive array.

For simplicity, assume an example of a square array of uniformly spaced transmitters and receivers 1, where the receivers lie on a N by N grid 2, at a spacing of d for both the horizontal and vertical directions. In this case, the transmitters illustrated in FIG. 1 would each be 2$d$ wide and 2$d$ high. High-resolution dynamic volumetric imaging, could, for example, require a 16 by 16 receiver array and hence an 8 by 8 array of 64 transmitters (N=16). The two-dimension amplitude pattern of a 2$d$ by 2$d$ square transmitter aperture is plotted as a function of x=(d/$\lambda$) sin ø in FIG. 2.

Since the receivers are not directive by themselves, suppression of grating lobes must be accomplished entirely by the transmitter pattern. Hence triangular shading can be used to produce a low-side lobe (sin $\pi x/\pi x)^2$ pattern in both x and y (corresponding to azimuth and elevation) This is illustrated in FIG. 3, (showing azimuth only) for the case of N=16.

For example, if f=4 MHz, then $\lambda$=c/f=1.540/4=0.385 mm. Making d slightly less than 1 mm (so that the receiver array is 1.5 cm by 1.5 cm), results in d/$\lambda \approx$2.5. Thus, in this example, the thinning is five to one, resulting in a reduction in the number of elements in the two dimensional array by a factor of 25.

Figure 3:
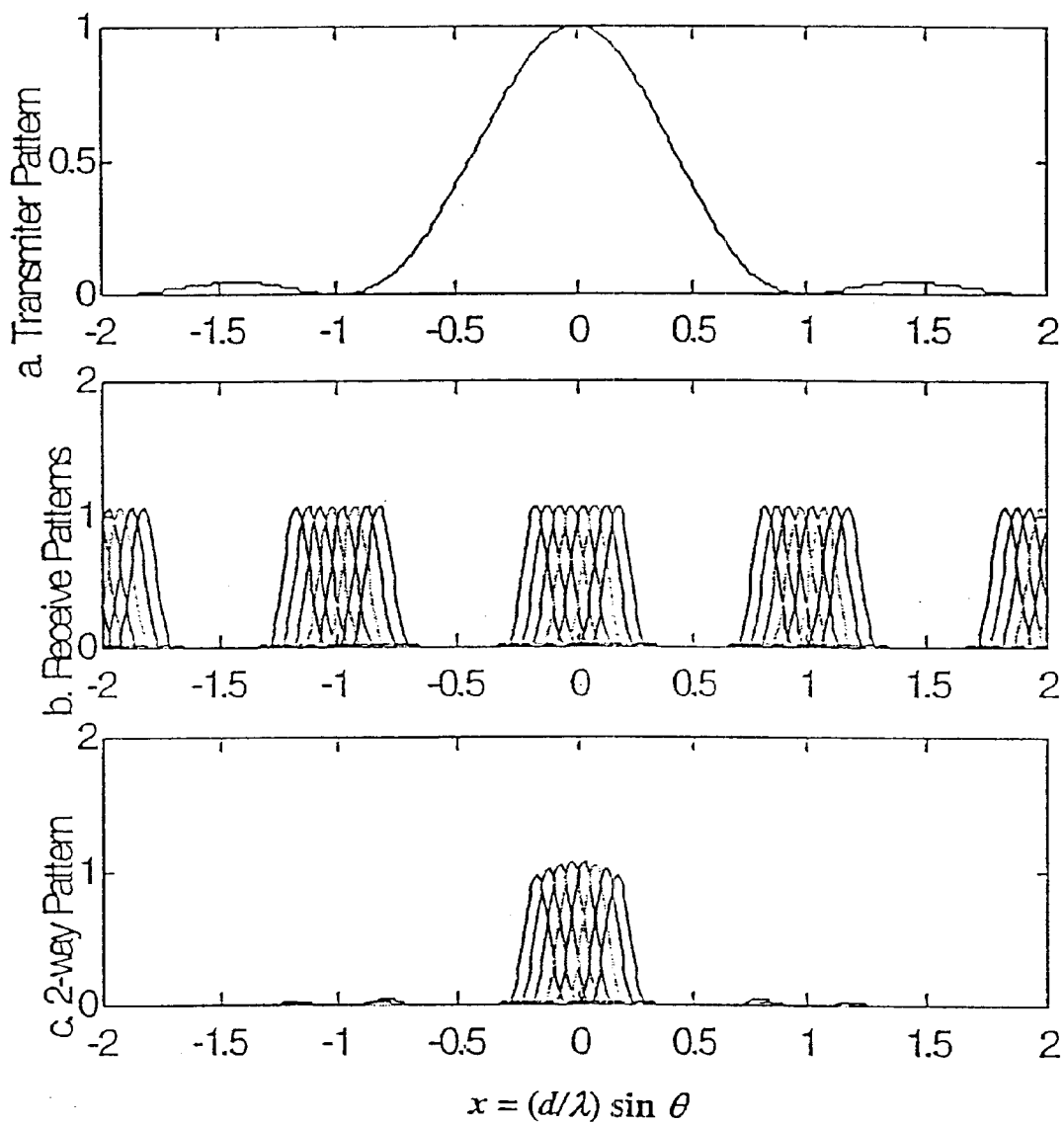
FIG. 3 plots one-dimensional patterns for a 16 element linear receive array and a two-element long transmitter (N=16 and r=2).

FIG. 3$a$ shows the transmitter pattern as a function of x. FIG. 3$b$ shows the pattern of a 16 element linear array, using Hanning weighting and steered to eight different values of x, with |x|<0.2. This corresponds to an 8×8 cluster of 64 receiver beams that are digitally produced for each transmitted pulse. Since there are 64 transmitters, each aimed and focused at a different region, 4096 lines are formed in only 64 pulses. This is one quarter the time it takes a conventional ultrasound imager to produce only 256 lines. Further, only 256 receiver elements and 64 transmitter apertures were used. The pulse generation, detection, signal processing and image generation functions are performed in an ultrasonic imaging device 8, well known in the art, with which the transducer 4 communicates over suitable cabling 9.

Figure 4:
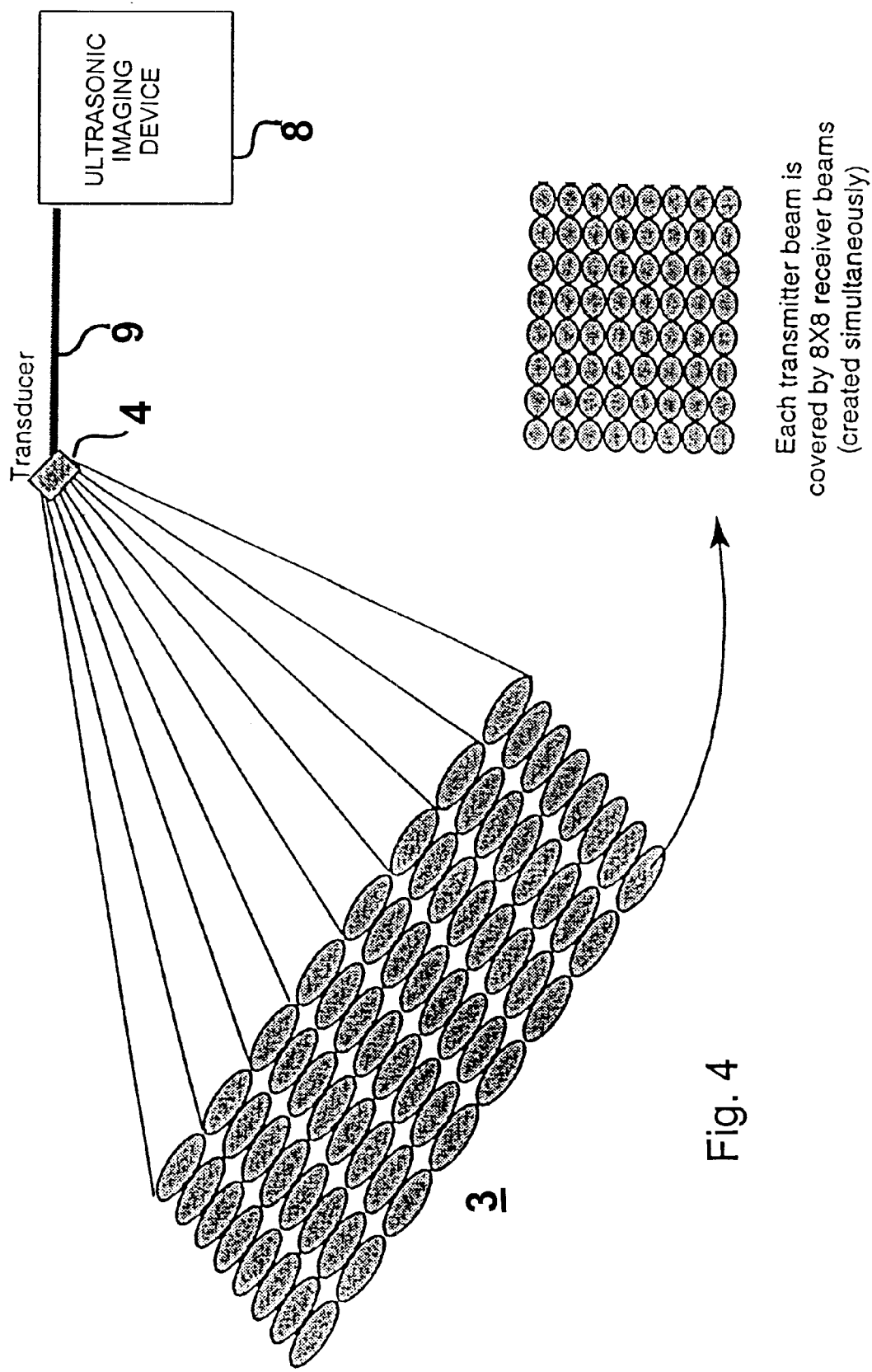
FIG. 4 is a representational view of an 8 by 8 array of transmitter beams, created sequentially by phase-shift controlling the elements of the transducer's phased array.

The resulting beam cluster is illustrated in azimuth only in FIG. 3c. In general, the origin (x=0) of FIG. 3 will be translated to correspond to the azimuth angle of the center of the current transmit beam. FIG. 4 shows the beam configuration 3 in two angular dimensions, where FIG. 3c is a horizontal cut through the receiver beams illustrated in FIG. 4. The additional measurement of time delay or depth (range) results in a 3-D image. The four to one reduction in imaging time allows for increased volumes per second for 3-D color flow imaging.

As explained above, conventional imagers view a single slice, with between 64 and 256 lines or beams. This invention views a three dimensional volume with a 64 by 64 array of lines in one quarter the time. The array, is bistatic. However, the transmitters and the receiver elements in the probe transducer 4 could be kept separate and the number of transmitters (and hence the total number of lines) can be doubled by filling in the blank spaces of FIG. 1b with another set of $(N/2)^2$ elements. By way of example, this doubles the number of transmit beams 3 in FIG. 4 (left hand side) so that 8192 beams are created using only 256 receiver elements. By doubling the overall size of the transmitter array, a total of 16,384 beams can be formed.

The signal processing utilized with a thinned array of the invention can be, for example, the processing described in Provisional Application Ser. No. 60/136,364. However, a thinned array of the present invention utilizes a set of electronically-aimed fixed-focus transmitters to extend the region imaged beyond the limit imposed by the necessity to avoid grating lobes of a thinned receiver array.

Figure 5:
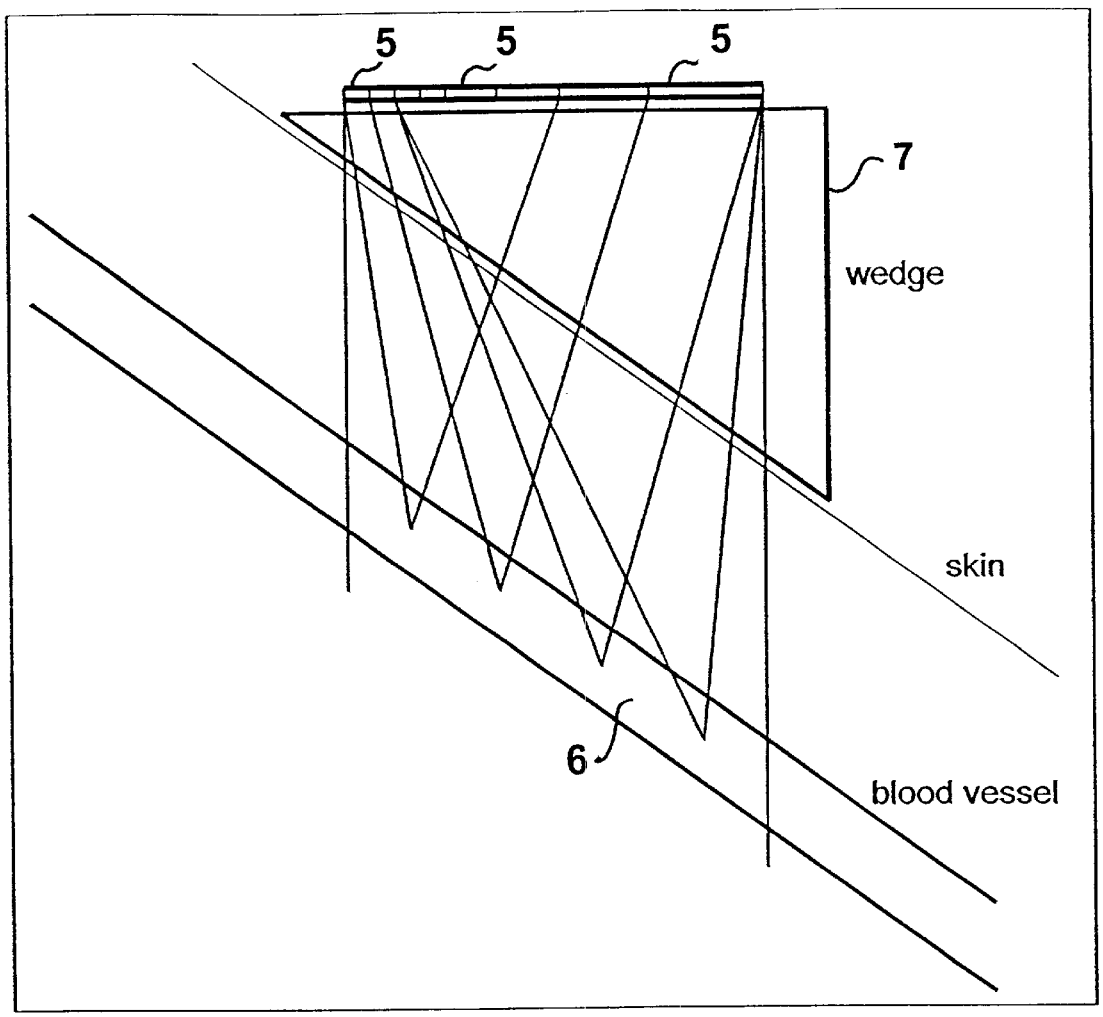
FIG. 5 is a schematic side view of a piezoelectric probe of the invention insonating a blood vessel through a layer of skin.
Figure 6:
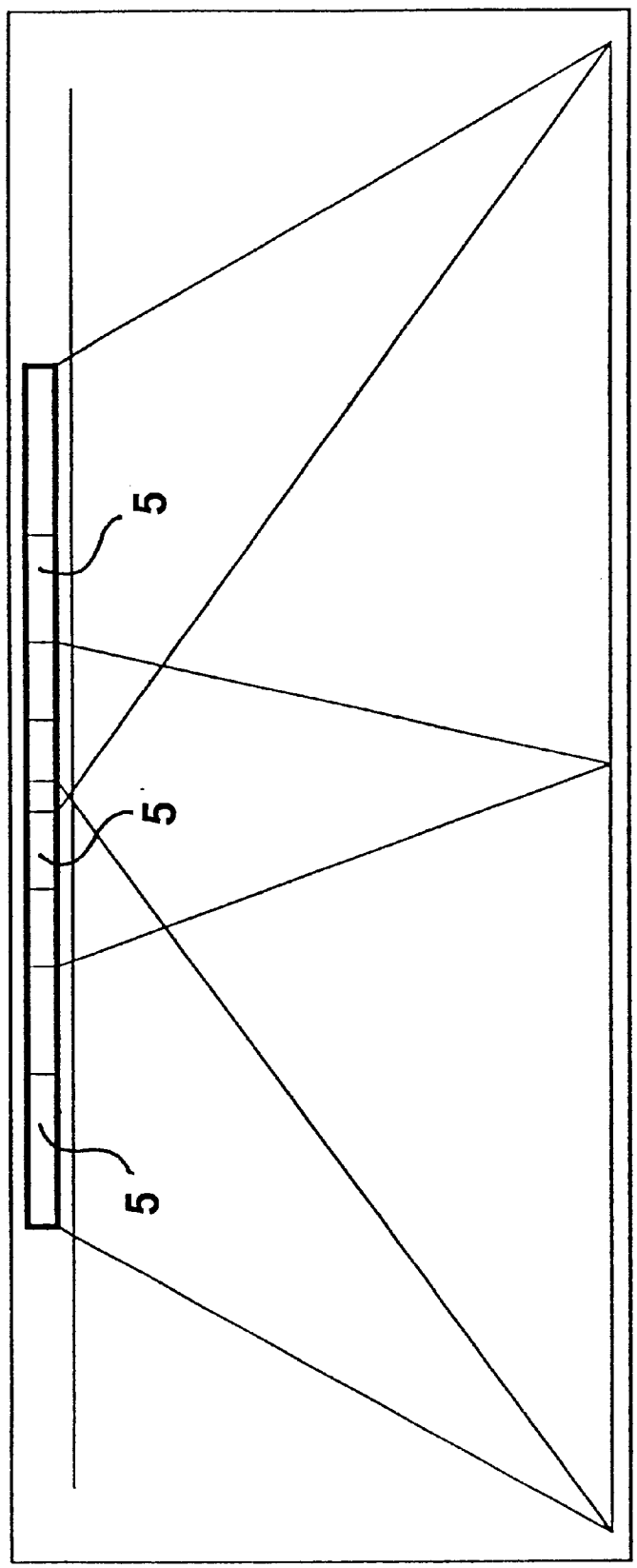
FIG. 6 is a schematic side view of an alternate probe geometry, showing the smallest piezoelectric elements at the center of the probe.

In this invention, we extend the field of view by varying the size of the elements. In one particular embodiment, the element size (and hence the spacing between elements) increases linearly. Typical situations are illustrated (for one dimension) in FIGS. 5 and 6. In FIG. 5, eight elements 5 are used to image a blood vessel 6. The first four elements ($n_0=4$) are equal in size ($d=d_0$) and the remaining four grow linearly with element number: $d=d_0+(n-n_0)s$ for $n>n_0$. In FIG. 5 a wedge 7 is used to attain a good Doppler angle because a thinned array is severely limited in the angle to which it can be steered. The primary purpose for using unequal element 5 sizes is that it increases that angle and hence extends the array's angular field of view, as shown in FIG. 6. Since greater angular resolution (and hence a larger array) is needed to maintain lateral resolution, it makes sense to increase the element 5 size with increasing range. At very short ranges, only a small number of elements are used and the array is linearly sequenced rather than steered. In FIG. 5 an example of sequencing would use elements #1, #2, and #3 (counting from the left) too examine the region near those elements centered near element #2, and elements #3, #4, and #5 to examine the next region. Sequencing, rather than steering is used in the "near field". FIG. 5 illustrates both sequencing and steering. Elements #1–6 are sequenced, as are #2–7 and #3–8. In addition, elements #3–8 are steered to a new focus by introducing phase shift into thje drive signals. Thus, the figure shows four focal points, but only the right-most is obtained by steering, as opposed to linear sequencing.

If all elements 5 were the same size, d, grating lobes would appear at values of $\lambda$ for which $(2\lambda d)(\sin \phi - \sin \phi_0)$ is an integer multiple of $2\lambda$. In the near field, the situation is even worse, in that grating lobes occur even for very small steering angles.

Figure 7:
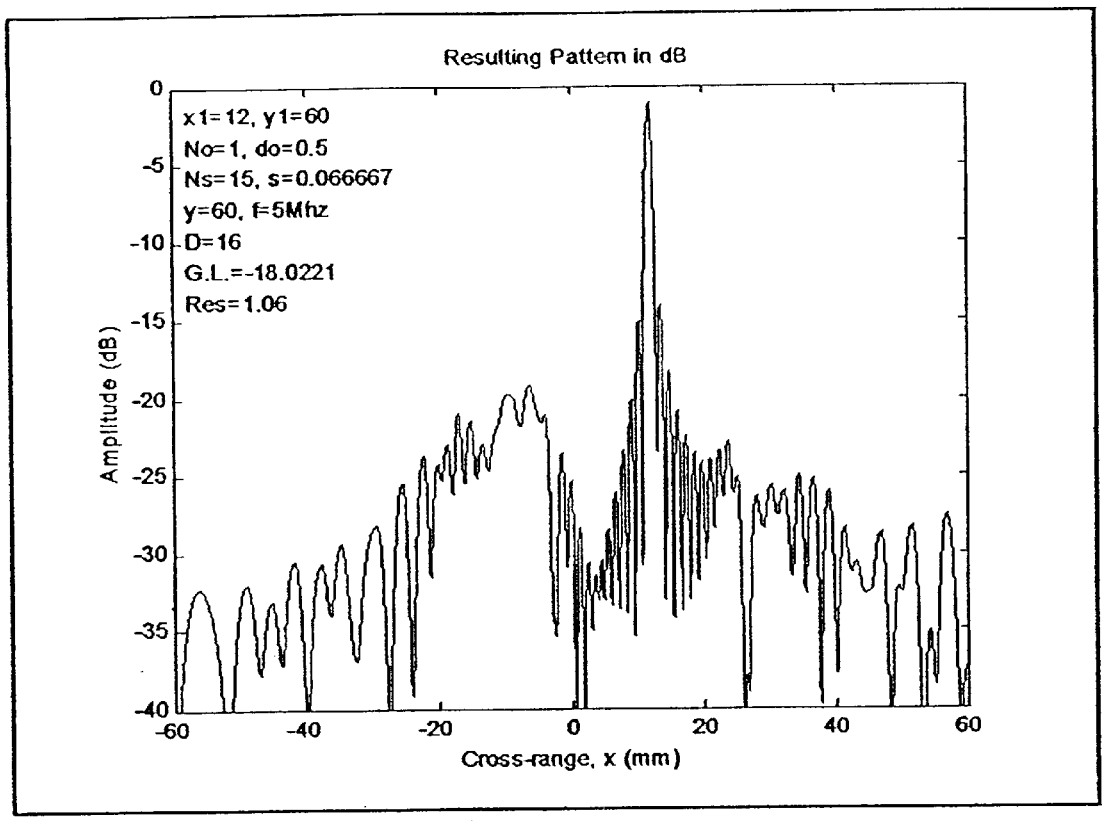
FIG. 7 is a graph showing an exemplary radiation of pattern from a filled thinned phased array probe with progressive element spacing.
Figure 8:
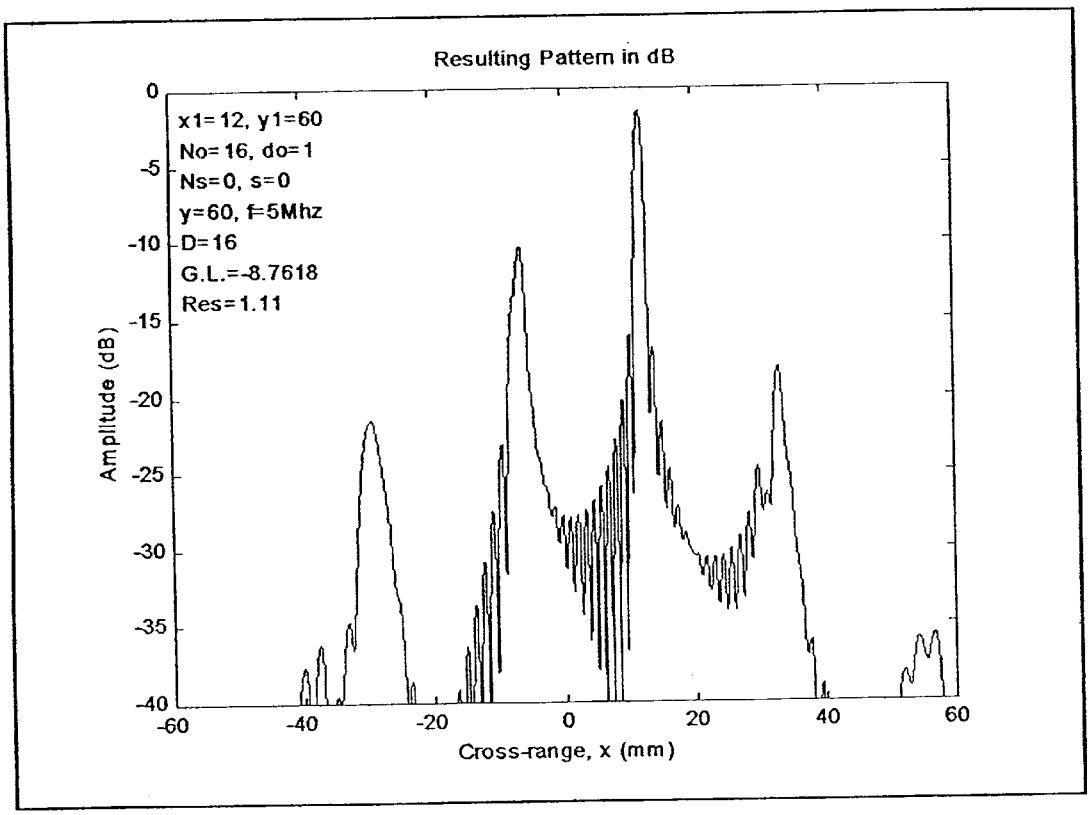
FIG. 8 is a graph showing an exemplary radiation of pattern from a filled thinned phased array probe with uniform element spacing.

FIG. 8 is a calculated signal pattern of a uniform linear array. FIG. 7 is a calculated signal pattern of an array with linear increasing element size. Both arrays are the same size and are focused at the same point. The peak grating lobe for the linear increasing element size array is 10 db below that of the uniform element size array.

What is claimed is:

1. A method for ultrasonic imaging of a volume of a subject using a piezoelectric probe consisting essentially of a two-dimensional thinned array of piezoelectric elements with progressive element sizing and an ultrasonic imaging device comprising:

a) transmitting a pulse of electrical energy at an ultrasonic frequency to at least a portion of the piezoelectric elements in a preselected order;

b) receiving a plurality of individual acoustic echo signals, one from each element of the array of piezoelectric elements subsequent to the pulsing of each element;

c) digitally analyzing and storing each of the acoustic signals until each element of the portion of piezoelectric elements has been pulsed, as a file of stored pulse data; and d) analyzing the data to produce the ultrasonic image; each echo signal containing Doppler frequency shift information related to the flow of a particulate fluid in the volume of the subject and the file of stored pulse data is analyzed by the ultrasonic imaging device to produce information related to the flow of the particulate fluid.

2. A method of claim 1 in which the subject is a living creature and the particulate fluid is blood.

3. A method of claim 2 in which the file of stored pulse data is analyzed to produce a representation of the three dimensional pattern of blood flow in the volume.

4. A method for ultrasonic imaging of a volume of a subject using a piezoelectric probe consisting essentially of a two-dimensional thinned array of piezoelectric elements with progressive element sizing and an ultrasonic imaging device comprising:

a) transmitting a pulse of electrical energy at an ultrasonic frequency to at least a portion of the piezoelectric elements in a preselected order;

b) receiving a plurality of individual acoustic echo signals, one from each element of the array of piezoelectric elements subsequent to the pulsing of each element;

c) digitally analyzing and storing each of the acoustic signals until each element of the portion of piezoelectric elements has been pulsed, as a file of stored pulse data; and d) analyzing the data to produce the ultrasonic image; the two dimensional thinned array comprising a contiguous subset of the smallest elements of uniform size and the acoustic signals received by the elements of the subset are analyzed to produce an ultrasonic image of a shallow portion of the volume adjacent to the piezoelectric probe.

* * * * *

UNITED STATES PATENT AND TRADEMARK OFFICE
CERTIFICATE OF CORRECTION

PATENT NO.    : 6,682,488 B2
DATED         : January 27, 2004
INVENTOR(S)   : Kenneth Abend It is certified that error appears in the above-identified patent and that said Letters Patent is hereby corrected as shown below:

<u>Title page,</u>
Item [73], Assignee, name should read -- Vuesonix Sensors, Inc. --

Signed and Sealed this

Twenty-first Day of June, 2005

JON W. DUDAS
*Director of the United States Patent and Trademark Office*